United States Patent [19]

Croll

[11] Patent Number: 4,919,616

[45] Date of Patent: Apr. 24, 1990

[54] DENTAL SPATULA WITH DISPLAY POSTS

[76] Inventor: Theodore P. Croll, 4232 Mechanicsville Rd., Mechanicsville, Pa. 18934

[21] Appl. No.: 398,524

[22] Filed: Aug. 25, 1989

[51] Int. Cl.$^5$ .......................... A61C 19/10; A61C 3/00
[52] U.S. Cl. ........................................ 433/26; 433/141
[58] Field of Search ................................... 433/26, 141

[56] References Cited

U.S. PATENT DOCUMENTS

| | | | |
|---|---|---|---|
| 3,507,042 | 4/1970 | Hana | 433/26 |
| 4,618,325 | 10/1986 | Appelle | 433/26 |
| 4,793,805 | 12/1988 | Pitre | 433/26 |
| 4,810,193 | 3/1989 | Wieder | 433/26 |

FOREIGN PATENT DOCUMENTS

| | | | |
|---|---|---|---|
| 2939211 | 4/1980 | Fed. Rep. of Germany | 433/141 |
| 2337541 | 8/1977 | France | 433/141 |

Primary Examiner—John J. Wilson
Attorney, Agent, or Firm—Gregory J. Gore

[57] ABSTRACT

A unique dental spatula includes an angle head, and an elongate body having a plurality of lateral projections forming apertured posts for affixing and displaying color-shade samples. The spatula portion of the instrument has an angled head so that the instrument can be conveniently held for spatulation or for holding the color samples adjacent to the patient's teeth to visually determine the proper color match. The elongate handle portion of the present invention is made of a clear material so that it does not affect resin coloration and further includes a roughened front surface for retaining written indicia, which serves to denote the particular proportions of material used in a given sample.

4 Claims, 2 Drawing Sheets

DENTAL SPATULA WITH DISPLAY POSTS

FIELD OF THE INVENTION

The present invention relates to dentistry and, more particularly, to instruments used by dentists in preparing chemical compositions for tooth restoration and coloration.

BACKGROUND OF THE INVENTION

Polymerized composite resins are commonly used in dentistry for restoring teeth. Achieving coloration matching of the restoration material is an advantage of these materials and, typically, two or more resins of different color shades are mixed to achieve a match between the blended material and the color of the restored tooth or other teeth approximal to the restoration site.

In achieving the proper color mixture, the resins are spatulated and then light-cured. The color sample is then compared with the patient's other teeth to confirm a proper color match. The mixing process is continued by trial and error until the proper proportions of resin colors are determined. This prior art process requires various separate instruments. There are no instruments providing a structure which conveniently aids the organization and recording of the trial and error color-shade matching process.

SUMMARY OF THE INVENTION

It is the purpose of the present invention to combine into a single instrument a variety of structures useful in the resin-mixing and color-matching procedure described above. This is achieved by way of a unique spatula having an angled head, and an elongate body having a plurality of lateral projections forming apertured posts for affixing and displaying color-shade samples. The spatula portion of the instrument has an angled head so that the instrument can be conveniently held for spatulation, or for holding the color samples adjacent to the patient's teeth to visually determine the proper color match. The elongate body of the present invention is made of a clear material so that it does not affect resin coloration and further includes a roughened front surface for retaining written indicia, which serves to denote the particular proportions of material used in a given sample.

Further objects and advantages of the present device will be readily apparent to those of ordinary skill in the art from the following drawings and description of the preferred embodiment.

DESCRIPTION OF THE PREFERRED EMBODIMENT

Figure 1:
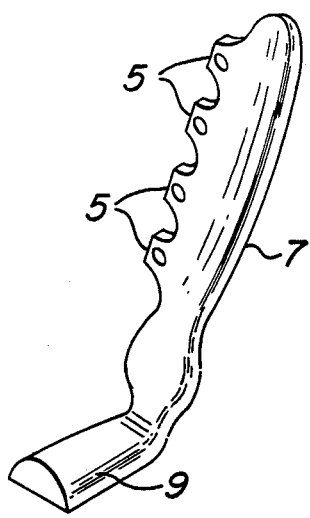
FIG. 1 is a top isometric view of the present dental spatula device.
Figure 2:
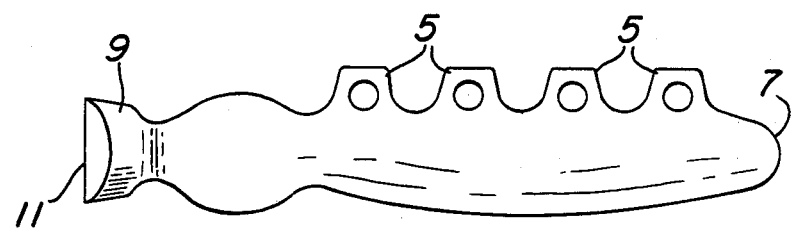
FIG. 2 is a front view of the present device.

Referring now to FIGS. 1 and 2, the spatula includes an elongate body 7 and angled spatula head 9. The spatula head includes a flat, back portion 11 and a raised front surface. The spatula head is angled with respect to the elongate body approximately 120 degrees. The elongate body contains a plurality of laterally projecting display posts 5 which are apertured front to back in order to aid the mechanical attachment of polymerized resin to the posts.

The instrument is preferably of unitary construction and made of a clear material, such as non-tinted methyl methacrylate, or a hard polyvinyl chloride. The instrument is necessarily transparent because any coloration of the device would affect its use as a color shade guide. Because the device can be made from inexpensive materials, it is intended to be disposable and used for one patient only. This affords the reassurance of a new antiseptic spatula with each use.

Figure 3:
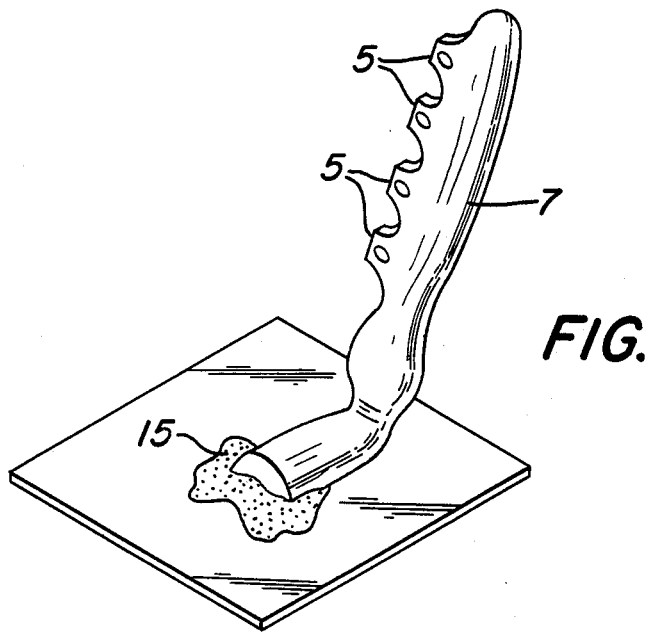
FIG. 3 is a top isometric view showing the position of the device during spatulation.
Figure 4:
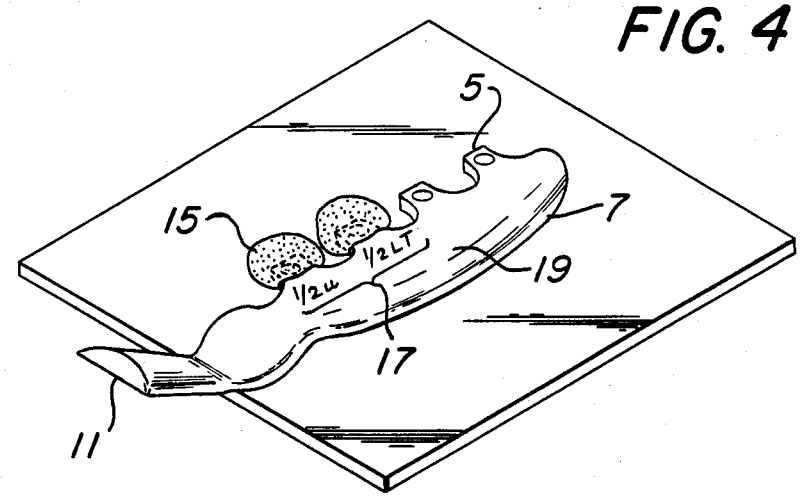
FIG. 4 is a top front isometric view showing resin material applied to the display posts.
Figure 5:
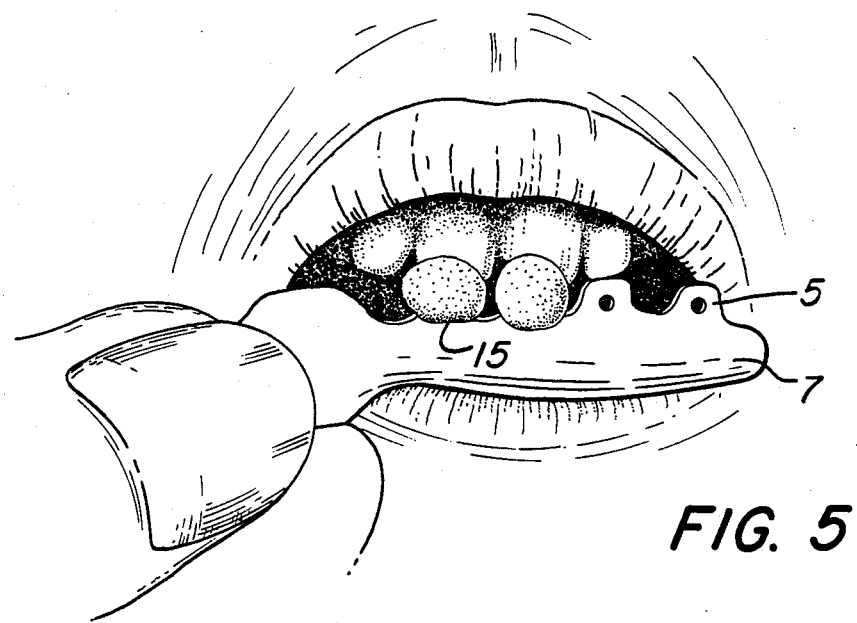
FIG. 5 is a front view showing the present device displaying samples of two different composite resins adjacent the patient's teeth to visually determine a color match.

The present spatula device is used as follows. As shown in FIG. 3, a trial composite resin mixture 15 is spatulated with the back side of the spatula head. Referring now to FIG. 4, the spatulated mixture 15 is applied to one of the posts 5 and polymerized in the usual manner. The roughened front surface of the spatula 19 is convenient for retaining a written notation, such as 17, which provides a reminder to the dentist of the exact mixture used to create the particular sample displayed on the post above. Referring now to FIG. 5, the spatula head portion also serves as a convenient angled handle for the dentist to hold the displayed polymerized samples adjacent to the patient's teeth for visual determination of the proper color match.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. A dental spatula for mixing and displaying composite resin samples, comprising:
   a. an elongate body which includes a plurality of laterally projecting display posts; and
   b. a spatula head at one end opposite said elongate body, said spatula head angled approximately 120 degrees with respect to said elongate body.

2. The dental spatula described in claim 1 further including apertures in each of said display posts for enhancing the mechanical attachment between polymerized resin materials and each post.

3. The dental spatula of claim 2 wherein the front surface of said elongate body is roughened to provide a surface to facilitate writing thereon.

4. The dental spatula of claim 3 wherein said spatula is of unitary construction and composed of a clear, synthetic material.

* * * * *